(12) United States Patent
Abboud et al.

(10) Patent No.: US 7,842,031 B2
(45) Date of Patent: *Nov. 30, 2010

(54) BIOIMPEDANCE MEASUREMENT SYSTEM AND METHOD

(75) Inventors: Marwan Abboud, Pierrefonds (CA); Johnny Al Asmar, Nicosia (CY); Chadi Harmouche, Petit St-Laurent (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 29 days.

This patent is subject to a terminal disclaimer.

(21) Appl. No.: 11/283,057

(22) Filed: Nov. 18, 2005

(65) Prior Publication Data

US 2007/0255162 A1 Nov. 1, 2007

(51) Int. Cl.
*A61B 18/18* (2006.01)
*A61B 5/05* (2006.01)
(52) U.S. Cl. ............... 606/20; 606/21; 606/22; 606/23; 600/547
(58) Field of Classification Search ............ 600/506, 600/547, 24–26; 606/20, 21, 23; 324/605
See application file for complete search history.

(56) References Cited

U.S. PATENT DOCUMENTS

| | | | |
|---|---|---|---|
| 4,587,975 A * | 5/1986 | Salo et al. ............ 600/506 |
| 4,860,744 A | 8/1989 | Johnson et al. | |
| 4,998,933 A | 3/1991 | Eggers et al. | |
| 5,057,105 A | 10/1991 | Malone et al. | |
| 5,069,223 A | 12/1991 | McRae | |
| 5,122,137 A | 6/1992 | Lennox | |
| 5,156,151 A | 10/1992 | Imran | |
| 5,184,621 A | 2/1993 | Vogel et al. | |
| 5,334,193 A | 8/1994 | Nardella | |
| 5,341,807 A | 8/1994 | Nardella | |
| 5,348,554 A | 9/1994 | Imran et al. | |
| 5,462,545 A | 10/1995 | Wang et al. | |
| 5,479,938 A | 1/1996 | Weier | |
| 5,500,011 A | 3/1996 | Desai | |
| 5,501,681 A | 3/1996 | Neuwirth et al. | |

(Continued)

FOREIGN PATENT DOCUMENTS

EP   0449401 A2   10/1991

(Continued)

*Primary Examiner*—Max Hindenburg
*Assistant Examiner*—John Pani
(74) *Attorney, Agent, or Firm*—Christopher & Weisberg, P.A.

(57) ABSTRACT

Methods and systems for detecting fluid egress, assessing lesion quality, determining tissue composition or structure, determining ice coverage of catheter tip and providing tissue contact assessment, by providing a catheter having a shaft with a proximal end portion and a distal end portion, the proximal end portion and the distal end portion define at least one fluid pathway therebetween with the shaft having a plurality of electrodes, positioning the catheter at a tissue treatment site, applying an electrical current between at least two of the plurality of electrodes, measuring impedance voltage between the at least two of the plurality of electrodes and, processing the measured impedance voltage caused by the applied electrical current to determine if fluid egress is present, to assess lesion quality, to determine tissue composition, ice cover of catheter tip, and to provide contact assessment. The system may have a control unit, a microprocessor, an impedance measuring device or the like to perform processing of impedance data.

5 Claims, 9 Drawing Sheets

U.S. PATENT DOCUMENTS

| | | | |
|---|---|---|---|
| 5,509,411 A | 4/1996 | Littmann et al. | |
| 5,549,109 A | 8/1996 | Samson et al. | |
| 5,555,883 A | 9/1996 | Avitall | |
| 5,596,995 A | 1/1997 | Sherman et al. | |
| 5,657,755 A | 8/1997 | Desai | |
| 5,673,704 A | 10/1997 | Marchlinski et al. | |
| 5,718,701 A | 2/1998 | Shai et al. | |
| 5,741,214 A | 4/1998 | Ouchi et al. | |
| 5,755,715 A | 5/1998 | Stern et al. | |
| 5,769,786 A | 6/1998 | Wiegel | |
| 5,771,895 A | 6/1998 | Slager | |
| 5,775,327 A | 7/1998 | Randolph et al. | |
| 5,836,990 A | 11/1998 | Li | |
| 5,869,971 A | 2/1999 | Sherman | |
| 5,891,027 A | 4/1999 | Tu et al. | |
| 5,947,910 A * | 9/1999 | Zimmet | 600/547 |
| 5,957,922 A | 9/1999 | Imran | |
| 6,016,437 A | 1/2000 | Tu et al. | |
| 6,030,379 A | 2/2000 | Panescu et al. | |
| 6,049,737 A | 4/2000 | Simpson et al. | |
| 6,064,905 A | 5/2000 | Webster, Jr. et al. | |
| 6,164,283 A | 12/2000 | Lesh | |
| 6,179,788 B1 | 1/2001 | Sullivan | |
| 6,190,378 B1 | 2/2001 | Jarvinen | |
| 6,217,573 B1 | 4/2001 | Webster | |
| 6,231,518 B1 | 5/2001 | Grabek et al. | |
| 6,235,018 B1 | 5/2001 | LePivert | |
| 6,241,754 B1 | 6/2001 | Swanson et al. | |
| 6,245,064 B1 | 6/2001 | Lesh et al. | |
| 6,245,599 B1 | 6/2001 | Goto et al. | |
| 6,254,598 B1 * | 7/2001 | Edwards et al. | 606/41 |
| 6,292,695 B1 | 9/2001 | Webster, Jr. et al. | |
| 6,325,797 B1 | 12/2001 | Stewart et al. | |
| 6,360,123 B1 * | 3/2002 | Kimchi et al. | 600/547 |
| 6,391,024 B1 | 5/2002 | Sun et al. | |
| 6,423,057 B1 | 7/2002 | He et al. | |
| 6,471,693 B1 | 10/2002 | Carroll et al. | |
| 6,551,274 B2 | 4/2003 | Heiner | |
| 6,551,309 B1 | 4/2003 | LePivert | |
| 6,569,158 B1 * | 5/2003 | Abboud et al. | 606/20 |
| 6,752,804 B2 | 6/2004 | Simpson et al. | |
| 6,761,716 B2 | 7/2004 | Kadhiresan et al. | |
| 7,070,594 B2 | 7/2006 | Sherman | |
| 7,442,190 B2 * | 10/2008 | Abboud et al. | 606/21 |
| 2002/0062124 A1 | 5/2002 | Keane | |
| 2002/0077627 A1 | 6/2002 | Johnson et al. | |
| 2003/0018326 A1 * | 1/2003 | Abboud et al. | 606/20 |
| 2005/0038422 A1 | 2/2005 | Maurice | |
| 2005/0177146 A1 | 8/2005 | Sherman | |
| 2005/0228367 A1 * | 10/2005 | Abboud et al. | 606/20 |
| 2006/0135953 A1 | 6/2006 | Kania et al. | |
| 2006/0200039 A1 * | 9/2006 | Brockway et al. | 600/547 |
| 2007/0255162 A1 | 11/2007 | Abboud et al. | |

FOREIGN PATENT DOCUMENTS

| | | |
|---|---|---|
| WO | WO 00/51683 | 9/2000 |
| WO | WO 00/67830 | 11/2000 |

* cited by examiner

BIOIMPEDANCE MEASUREMENT SYSTEM AND METHOD

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a system and method for treating tissue using cooled medical devices using electrical impedance measurements with the device.

BACKGROUND OF THE INVENTION

Effectiveness of cryotreatment of endocardial tissue is significantly affected by the contact of the catheter tip or thermally transmissive region to the tissue. Ex-vivo studies show a correlation between the lesion sizes created and the tip or thermally-transmissive region to tissue contact quality. A larger lesion size can be achieved with the same device by improving the tip to tissue pressure or contact. Various methods have been used to assess tip or thermally-transmissive region contact, using RF catheters and/or ultrasound imaging. However, none of these methods has proved entirely satisfactory.

The problem extends to all areas of tissue treatment wherein the tissue undergoes some change or "physiological event" during the course of treatment. In addition to contact quality assessment, in treatment devices that employ fluid flows, detection and containment of leaks is a critical problem, especially in the operation of cryogenic devices for therapeutic purposes, lest a leak of coolant enter the body and thereby cause significant harm. Known catheters which employ inflatable balloons often inflate the balloons to relatively high pressures that exceed the ambient pressure in a blood vessel or body lumen. However, to contain the coolant, these catheters generally employ thicker balloons, dual-layered balloons, mechanically rigid cooling chambers, and other similar unitary construction containment mechanisms. These techniques however, lack robustness, in that if the unitary balloon, cooling chamber, or other form of containment develops a crack, leak, rupture, or other critical structural integrity failure, coolant may egress from the catheter. To minimize the amount and duration of any such leaks, it is desirable to use a fluid detection system that detects a gas or liquid expulsion or egress from the catheter shaft and signals a control unit to halt the flow of cryogenic fluid.

Furthermore, since many treatment systems and methods are applied in internal body lumens, organs or other unobservable tissue regions, the orientation and attitude of the device structure relative to the tissue is of significant importance in ensuring the effective and efficient treatment of tissue. This applies to many tissue treatment systems, both surgical and non-surgical, using a variety of modalities, including cooling through cryotreatment, heat or electrically induced heating, ultrasound, microwave, and RF, to name a few.

This collection of problems may be resolved in part by developing a specialized transducer suitable for the "body" environment in which it operates. For many physiological events, there is no specialized transducer. The events in question include changes in the natural state of tissue, such as temperature, dielectric or conductivity changes, structural changes to the cells and cell matrix, dimensional changes, or changes in the operation of, or interplay between, tissue regions and/or foreign bodies, such as blood flow in an artery having a treatment device inserted therein.

All of these changes may be correlated to, or affected by, relative changes in the bioelectrical impedance of the tissue region.

It would be desirable to provide an apparatus and method of assessing lesion quality, monitoring and detecting any occurrences of fluid egress, determining blood vessel occlusion, determining tissue composition as well as assessing the quality of the contact between the tip or thermally-transmissive region of a cryogenic device and the tissue to be treated.

SUMMARY OF THE INVENTION

The present invention advantageously provides methods and systems for detecting fluid egress, assessing lesion quality, determining tissue composition or structure, and providing tissue contact assessment.

In an exemplary embodiment, a method is provided for detecting fluid egress including the steps of positioning a catheter at a tissue treatment site, where the catheter includes a shaft, which has a proximal end portion and a distal end portion, wherein the proximal end portion and the distal end portion define at least one fluid pathway between the distal end portion and the proximal end portion, and the shaft has a plurality of electrodes, applying an electrical current between at least two of the plurality of electrodes, measuring impedance voltage between the at least two of the plurality of electrodes and, processing the measured impedance voltage resulting from the applied electrical current to determine if fluid egress is present.

The processing step of the method for detecting fluid egress may include the steps of establishing a normal impedance voltage range, monitoring to determine if the impedance voltage varies outside of the impedance voltage range, and generating a signal if the impedance voltage measurement varies outside of the impedance voltage range. A control unit, a microprocessor, an impedance-measuring device or the like may perform the processing step. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

In another exemplary embodiment, a method is provided for accessing lesion quality including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes a first electrode and a second electrode, and measuring a baseline impedance, activating the catheter such that the treatment portion cools the tissue, applying an electrical current between the first and second electrodes, and processing the measured impedance voltage caused by the applied electrical current to determine the amount of treated tissue after each activation of the catheter.

The processing step of the method for accessing lesion quality may be performed by a control unit, a microprocessor, an impedance measuring device or the like. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

In still another exemplary embodiment, a method is provided for accessing tissue composition including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes a first electrode and a second electrode, activating the catheter such that the treatment portion cools the tissue, applying an electrical current between the first and second electrodes, measuring a impedance voltage between the first and second electrodes, and processing the measured impedance caused by the applied electrical current, establishing a normal impedance range for a tissue type, monitoring the impedance to determine if the impedance varies into a tissue type impedance range, and generating an impedance signal that can be processed to identify the tissue type impedance range.

The processing step of the method for accessing tissue composition may be performed by a control unit, a microprocessor, an impedance measuring device or the like. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

In still another exemplary embodiment, a method is provided for accessing tissue composition including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes a first electrode and a second electrode, activating the catheter such that the treatment portion cools the tissue, applying an electrical current between the first and second electrodes, measuring a impedance voltage between the first and second electrodes, and processing the measured impedance caused by the applied electrical current, delivering coolant to the treatment tip, measuring a second impedance voltage between the first and second electrodes, processing the measured impedance voltage caused by the applied electrical current to determine a delta impedance from the first and second impedances, and determining if the delta impedance has reached a maximum value.

The processing step of the method for accessing tissue composition may be performed by a control unit, a microprocessor, an impedance measuring device or the like. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

A system and method for detecting fluid egress including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes at least four electrodes, a first pair of electrodes and a second pair of electrodes, applying an electrical current between the first pair of electrodes, measuring a impedance voltage between the second pair of electrodes, and processing the measured impedance voltage caused by the applied electrical current to determine if fluid egress is present.

The number and location of the electrodes will affect the system measurement sensitivity. For example, as the distance between the pair of measurement electrodes is decreased, the system measurement sensitivity is increased. On the other hand, as the distance between the pair of measurement electrodes and the pair of excitation current electrodes is decreased, the system measurement sensitivity is decreased. In another embodiment, where a catheter having a single pair of electrodes for both measuring impedance and providing the excitation current, the system measurement sensitivity is also decreased.

The processing step of the method for detecting fluid egress may include the steps of establishing a normal impedance voltage range, monitoring to determine if the impedance voltage varies outside of the impedance voltage range, and generating a signal if the impedance voltage measurement varies outside of the impedance voltage range. A control unit, a microprocessor, an impedance-measuring device or the like may perform the processing step. In another embodiment of the method, the treatment portion of the catheter may include a cooling chamber in fluid communication with the at least one fluid pathway and having one of each pair of electrodes located near the distal side of the cooling chamber, and one of each pair of electrodes located near the proximal side of the cooling chamber.

In addition, a system and method for accessing lesion quality including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes a first electrode and a second electrode, activating the catheter such that the treatment portion cools the tissue, applying an electrical current between the first and second electrodes, measuring a impedance voltage between the first and second electrodes, and processing the measured impedance voltage caused by the applied electrical current to determine the amount of treated tissue after each activation of the catheter.

The processing step of the method for accessing lesion quality may be performed by a control unit, a microprocessor, an impedance measuring device or the like. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

In addition, a system and method for accessing tissue composition including the steps of positioning a catheter at a tissue treatment site, where the catheter includes a shaft, which has a proximal end portion and a distal end portion, wherein the proximal end portion and the distal end portion define at least one fluid pathway therebetween, and the shaft has a treatment portion that includes a first electrode and a second electrode, activating the catheter such that the treatment portion cools the tissue, applying an electrical current between the first and second electrodes, measuring a impedance voltage between the first and second electrodes, and processing the measured impedance caused by the applied electrical current, establishing a normal impedance range for a tissue type, monitoring the impedance to determine if the impedance varies into a tissue type impedance range, and generating a signal when the impedance varies into the identified tissue type impedance range.

The processing step of the method for accessing tissue composition may be performed by a control unit, a microprocessor, an impedance measuring device or the like. In another embodiment of the method, the treatment portion of catheter may include a cooling chamber in fluid communication with the at least one fluid pathway and having the first electrode located near the distal side of the cooling chamber, and the second electrode located near the proximal side of the cooling chamber.

As many treatment systems and methods are applied in internal body lumens, organs or other unobservable tissue regions, the orientation and attitude of the device structure relative to the tissue is of significant importance in ensuring the effective and efficient treatment of tissue. This applies to many tissue treatment systems, both surgical and non-surgical, using a variety of modalities, including cooling through cryotreatment, heat or electrically induced heating, ultrasound, microwave, and RF, to name a few.

Many of these events include changes in the natural state of tissue, such as temperature, dielectric or conductivity changes, structural changes to the cells and cell matrix, dimensional changes, or changes in the operation of, or interplay between, tissue regions and/or foreign bodies, such as blood flow in an artery having a treatment device inserted therein. All of these changes may be correlated to, or affected by, relative changes in the bio-impedance of the tissue region.

When using the term impedance, we are referring to the generally accepted definition of the term: a complex ratio of sinusoidal voltage to current in an electric circuit or component, except that as used herein, impedance shall apply to any region or space through which some electrical field is applied and current flows, and as used herein the terms "impedance" and "impedance voltage" are used synonymously. The impedance, Z, may be expressed as a complex number, $Z=R+jX$, wherein R is the resistance in real number ohms, X is the reactance in imaginary number ohms, and j is a multiplier that is the positive square root of negative one (−1).

Resistance, denoted R, is a measure of the extent to which a substance opposes the movement of electrons among its atoms. The more easily the atoms give up and/or accept electrons, the lower the resistance. Reactance denoted X, is an expression of the extent to which an electronic component, circuit, or system stores and releases energy as the current and voltage fluctuate with each AC (alternating current) cycle. Reactance is expressed in imaginary number ohms. It is observed for AC, but not for DC (direct current). When AC passes through a component that contains reactance, energy might be stored and released in the form of a magnetic field, in which case the reactance is inductive (denoted $+jX_L$); or energy might be stored and released in the form of an electric field, in which case the reactance is capacitive (denoted $-jX_C$). The impedance Z may be positive or negative depending on whether the phase of the current lags or leads on that of the voltage. Impedance, sometimes called "apparent resistance", is different from general resistance, in that impedance applies only to AC; however resistance R applies to both AC and DC, and is expressed in positive real number ohms.

As mentioned in the background section, the collection of problems may be resolved in part by developing a specialized transducer suitable for the "body" environment in which it operates. However, for many physiological events, there is no specialized transducer. The events in question include changes in the natural state of tissue, such as temperature, dielectric or conductivity changes, structural changes to the cells and cell matrix, dimensional changes, or changes in the operation of, or interplay between, tissue regions and/or foreign bodies, such as blood flow in an artery having a treatment device inserted therein. Using simple transducers, such as electrodes properly positioned in the tissue, the impedance between them is measured, which may depend on seasonal variations, blood flow, cardiac activity, respired volume, nervous activity, galvanic skin reflex, blood pressure, and salivation, to name a few. In some cases the measured impedance may be dissected into its resistive and reactive components. In other cases the total impedance may be measured, with or without resolution into its components, which may contain sufficient information on the physiological event, especially when measured relative to some reference or "baseline" impedance prior to the physiological event.

Additionally, during the operation of a medical device in a therapeutic procedure, such as in a blood vessel, the heart or other body organ, the medical user desires to establish a stable and uniform contact between the tip or thermally-transmissive region of the cryogenic device and the tissue to be treated (e.g., ablated). In those instances where the contact between the tip or thermally-transmissive region of the cryogenic device and the tissue to be treated is non-uniform or instable, the resulting ablation or lesion may be less than optimal. It is desirable for the medical professional to assess the state of the contact between the tip or thermally-transmissive region of the cryogenic device and the tissue to be treated, so that appropriate adjustments can be made to re-position the cryogenic device to obtain a more optimal contact and thus a more effective treatment.

In view of the proceeding, the present invention advantageously provides methods and systems for detecting fluid egress, assessing lesion quality, determining tissue composition and structure, determining ice coverage of catheter tip as well as providing tissue contact assessment.

Figure 1:
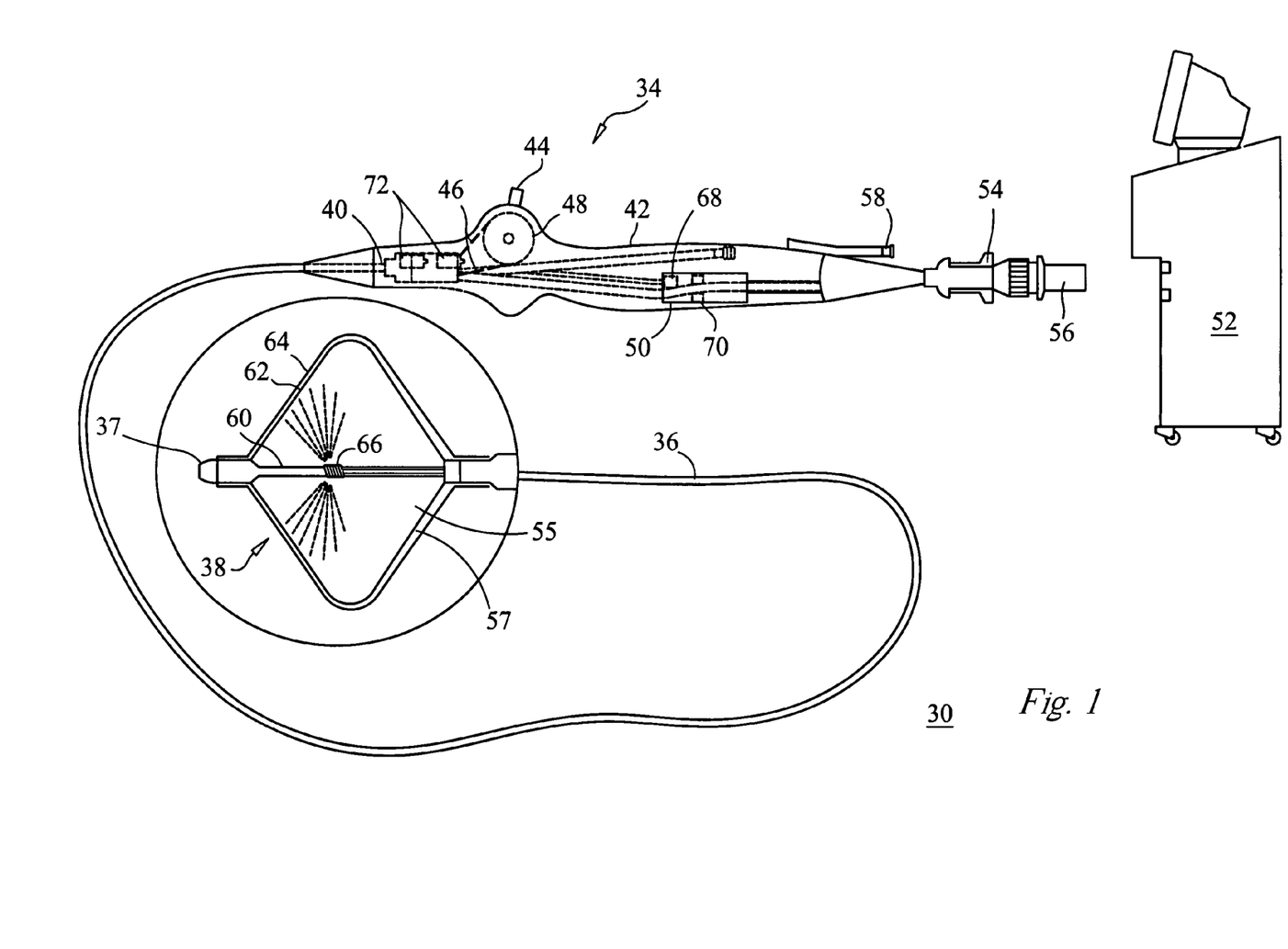
FIG. 1 illustrates a catheter system having an expandable thermally-transmissive region.

FIG. 1 illustrates an exemplary system 30 for performing cryogenic ablation. The system 30 includes an elongate, highly flexible ablation catheter 34 that is suitable for passage through the vasculature. The ablation catheter 34 includes a catheter body 36 having a distal end 37 with a thermally conductive region 38 at or proximal to the distal end 37. The distal end 37 and the thermally conductive region 38 are shown magnified and are described in greater detail below. The catheter body 36 has a proximal end 40 that is mated to a handle 42 that can include an element such as a lever 44 or knob for manipulating the catheter body 36 and the thermally conductive region 38. In the exemplary embodiment, a pull wire 46 with a proximal end and a distal end has its distal end anchored to the catheter at or near the distal end 37. The proximal end of the pull wire 46 is anchored to an element such as a cam 48 in communication with and responsive to the lever 44. The handle 42 can further include circuitry 50 for identification and/or use in controlling of the ablation catheter 34 or another component of the system 30.

Continuing to refer to FIG. 1, the handle 42 can also include connectors that are matable directly to a cryogenic fluid supply/exhaust and control unit or indirectly by way of one or more umbilicals. In the system illustrated, the handle 42 is provided with a first connector 54 that is matable with a co-axial fluid umbilical (not shown) and a second connector 56 that is matable with an electrical umbilical (not shown) that can further include an accessory box (not shown). In the exemplary system the fluid supply and exhaust, as well as various control mechanisms for the system are housed in a single console 52. In addition to providing an exhaust function for the ablation catheter fluid supply, the console 52 can also recover and/or re-circulate the cooling fluid. The handle 42 is provided with a fitting 58 for receiving a guide wire (not shown) that is passed into a guide wire lumen 60. During balloon inflation, contrast solution may be injected through the catheter's inner guide wire lumen 60 and into the pulmonary vein.

Still referring to FIG. 1, the thermally conductive region 38 is shown as a double balloon having a first membrane (e.g., inner balloon) 62 contained or enclosed within a second membrane (e.g., outer balloon) 64, thereby defining an interface or junction 57 between the first and second membranes. The second membrane 64 provides a safeguard to prevent fluid from leaking out of the cooling chamber 55 and into surrounding tissue should the first membrane 62, and therefore the cooling chamber 55, rupture or develop a leak. The junction 57 between the first and second membranes 62, 64 may be substantially under a vacuum, such that the first and second membranes 62, 64 are generally in contact with each other, with little or no open space between them. A coolant supply tube 66 in fluid communication with the coolant supply in the console 52 is provided to release coolant from one or more openings in the tube within the inner balloon 62 in response to console commands and other control input. A vacuum pump in the console 52 creates a low-pressure environment in one or more lumens within the catheter body 36 so that coolant is drawn into the lumen(s), away from the inner balloon 62, and towards the proximal end of the catheter body. The vacuum pump is also in fluid communication with the interface or junction 57 of the inner and the outer balloons 62, 64 so that any fluid that leaks from the inner balloon 62 is contained and aspirated.

Still referring to FIG. 1, the handle 42 includes one or more pressure sensors 68 to monitor the fluid pressure within one or both of the balloons, the blood detection devices 70 and the pressure relief valves 72. When coolant is released into the inner balloon 62, the inner and the outer balloon 64 expand to a predetermined shape to present an ablation surface, wherein the temperature of the ablation surface is determined by the material properties of the specific coolant selected for use, such as nitrous oxide, along with the pressure within the inner balloon 62 and the coolant flow rate.

Figure 2:
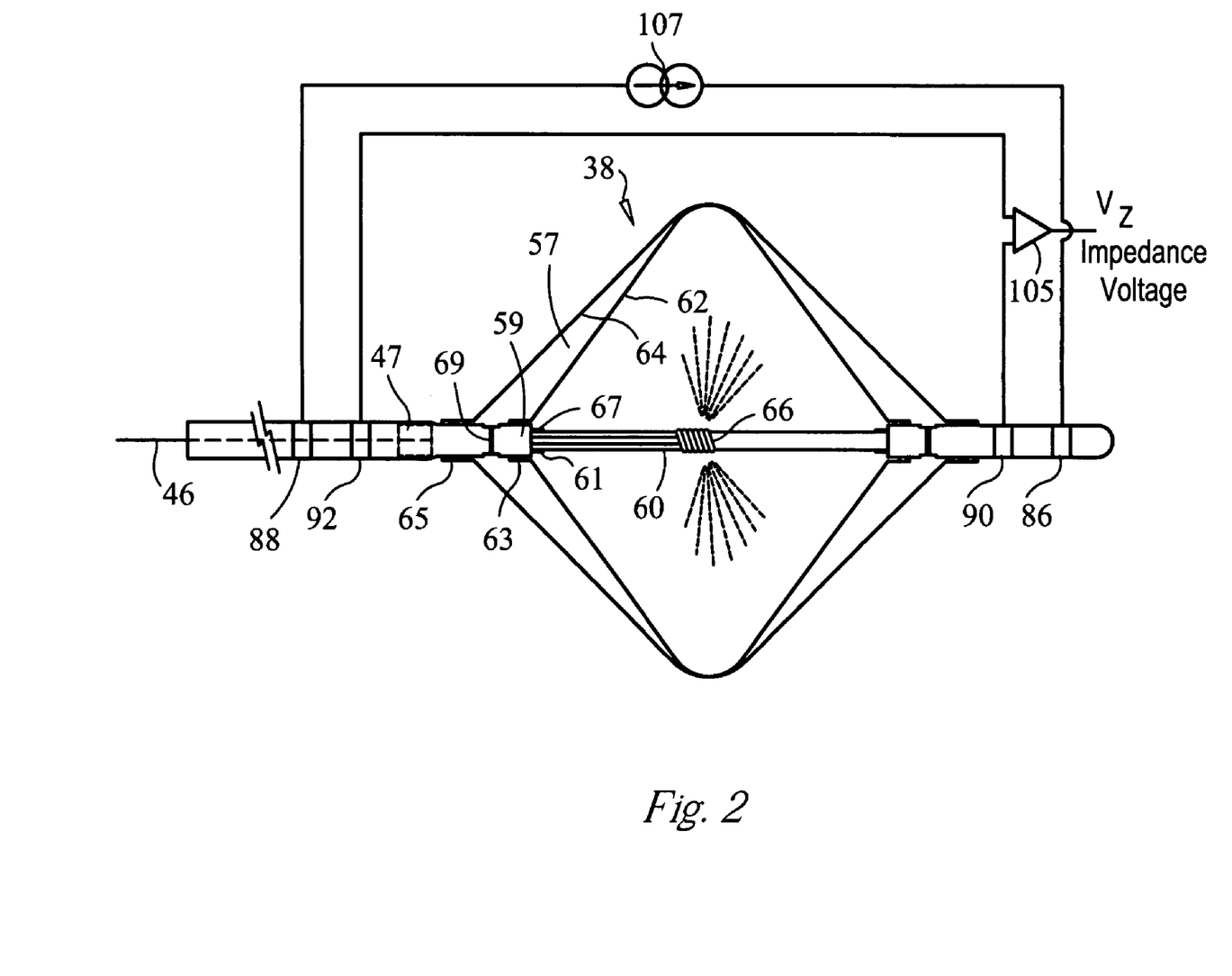
FIG. 2 illustrates an embodiment of a shaft of the catheter system of FIG. 1.

FIG. 2 illustrates an embodiment of a shaft or catheter body 36 of the balloon catheter system 34 of FIG. 1. The catheter body 36 includes a mounting section 59 in communication with the proximal end of thermally conductive element 38. The inner balloon 62 and outer balloon 64 are bonded to the mounting section 59. In this embodiment, the inner balloon 62 and outer balloon 64 are bonded at different locations, which are defined as the inner balloon bond joint 63 and the outer bond joint 65, however they may be bonded at the same bond joint. Additionally, several sensors are identified including a temperature sensor 61 (e.g., thermocouple wire), leak detectors 67, 69 (e.g., leak detection wires) and electrodes 86, 88, 90 and 92. In this embodiment, contact assessment, lesion quality, fluid egress and/or tip ice coverage may be provided by using a first pair of electrodes (86, 88); providing the excitation current 107 of well-selected amplitude (e.g., in the range of 0.2 mA to 5 mA) and frequency (e.g., in the range of 250 Hz to 500 kHz) to create a current field and measuring the differential impedance voltage as produced across a second pair of electrodes (90, 92).

In another embodiment of the catheter having a single pair of electrodes (e.g., 90 and 92) with one of the pair of electrodes located on the distal side of the thermally-transmissive region 38 (e.g., a single balloon), and the other of the pair located on the proximal side of the thermally-transmissive region 38, an excitation current 107 of well-selected amplitude and frequency is applied between the two electrodes to create a current field and measure the differential impedance voltage as produced across the same electrodes to determine tissue contact assessment, lesion quality and/or blood occlusion assessment. The processing algorithms and related aspects will be discussed in more detail below.

Figure 2A:
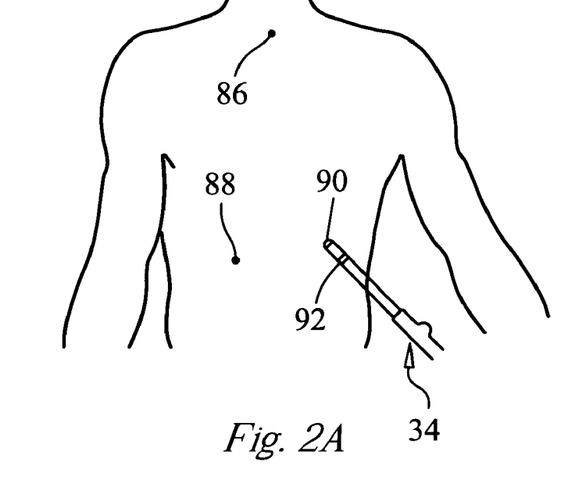
FIG. 2A illustrates an embodiment of the catheter system used with a pair of excitation electrodes positioned on a patient's body.

In another embodiment, as illustrated in FIG. 2A, a pair of excitation current electrodes (86, 88) are located on a patient's body and create an electrical field (i.e., polarize the patient's body), and the pair of measurement electrodes (90, 92) are located on the catheter 34. The tissue contact assessment, lesion quality and fluid egress aspects can be determined by applying an excitation current 107 of a well-selected amplitude and frequency to create a current field and measuring the differential impedance voltage as produced across the pair of electrodes (90, 92).

Figure 3:
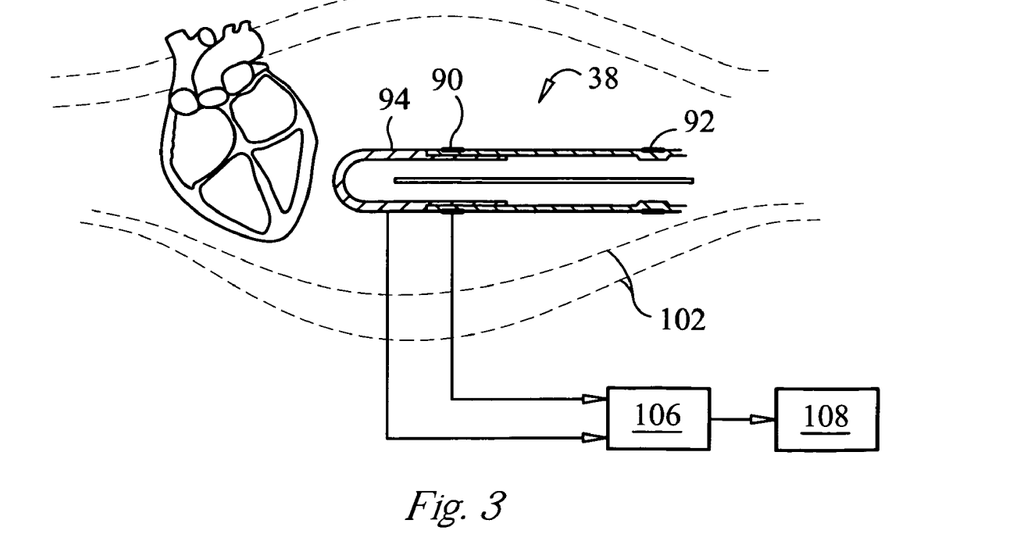
FIG. 3 illustrates a catheter system having a non-expandable thermally-transmissive region.

After applying an excitation current to the two electrodes 90, 92, the impedance voltage can be measured by the impedance measurement system 106 (as shown in FIG. 3). The impedance measurement signal is then processed using a signal processor 108 (as shown in FIG. 3), which extracts relevant data from a specific frequency range to correlate the impedance change to, for example, occlusion of a pulmonary vein. The signal processor 108 may be a standalone unit or it may be part of the control unit 52, the impedance measurement system 106 or another portion of the catheter system. The electrical impedance of the tissue is much higher than the impedance of the blood, so measuring the impedance between the first electrode 90 and the second electrode 92 would indicate the efficacy of a thermally conductive element to tissue contact. With high measurement sensitivity, the system should be able to quantify the contact quality. The impedance measurement system 106 provides information about the baseline impedance that may change as the balloon 38 occludes a vessel, such as a pulmonary vein (PV). As the balloon will occlude or stop the blood flow between the proximal side and the distal side of the balloon, the impedance at a defined frequency will increase, which provides an indication of the quality of the contact between the balloon 38 and the treatment tissue.

FIG. 3 illustrates another embodiment of the thermally conductive region 38 of catheter 34 positioned near a treatment tissue site, such as the heart. In this embodiment the thermally conductive region 38 is shown as having a thermally conductive non-balloon element. Although this embodiment is shown with a single thermally conductive element (e.g., tip 94), the thermally conductive region 38 may have two or more thermally conductive elements. An excitation current of well-selected amplitude and frequency is applied to the electrodes 90, 92 and tip electrode 94; the impedance (voltages) can be measured by the impedance measurement system 106 (e.g., between the tip electrode 94 and the electrode 90). Once the excitation current is applied to the electrodes it will produce the electrical current lines 102, which indicate overall field strength. The excitation field provides for or enables the polarization of the tissue or treatment area of the patient. The shape and density of the current lines 102 will characteristically result from the number and placement of the electrodes. The number and placement of the electrodes will determine the overall system sensitivity. Normally, a greater sensitivity is required to perform fluid egress detection as opposed to tissue contact assessment or tip ice formation.

In general, the detection of catheter fluid egress and of catheter tissue contact assessment may be determined using the same catheter and electrode configurations. The process for determining fluid egress and tissue contact assessment, typically may be determine by the selection of the excitation current applied to the catheter system. For example, if a gas bubble leak occurs in the catheter, a low frequency excitation current (e.g., in the range of 250 Hz to 100 kHz) can improve the detection of the gas bubble leak since the low frequency signal will not penetrate the gas bubble and the gas bubble will interrupt the electrical lines 102, and thus cause a spike in the measured impedance Z. On the other hand, if a high frequency excitation current (e.g., in the range of 20 kHz to 500 kHz) is applied, the high frequency excitation current will penetrate the gas bubble and therefore the gas bubble will not interrupt the electrical lines 102, causing the bubble to go undetected. Therefore, there are certain circumstances where additional electrodes may be necessary to improve the sensitivity of the overall detection system and process to improve leak detection/fluid egress.

Figure 3A:
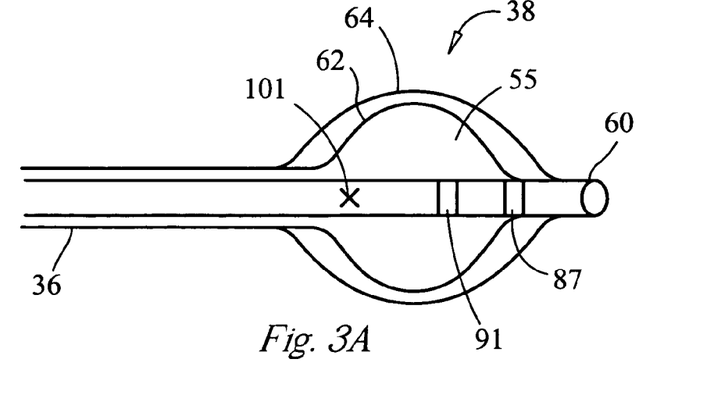
FIG. 3A illustrates a catheter system having measurement electrodes on the inside of a guidewire lumen.
Figure 3B:
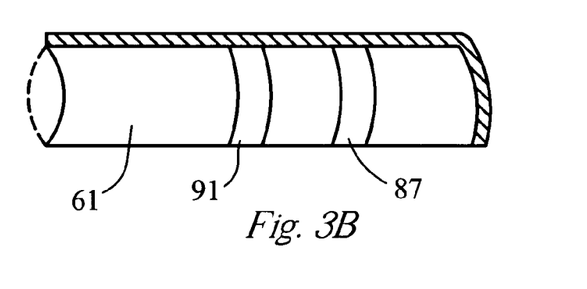
FIG. 3B illustrates a cutaway view of the guidewire lumen of FIG. 3A.

FIGS. 3A and 3B illustrate another embodiment of the thermally conductive region 38 of catheter 34. In this embodiment, the location of the measurement electrodes (87 and 91) is inside the guide wire lumen 60. In this embodiment, the inner member 62 and outer member 64 are connected to the catheter shaft 36 and define the cooling chamber 55. By locating the, measurement electrodes (87 and 91) on the inside of guide wire lumen 60, a fluid leak 101 from the catheter shaft 36 or guide wire lumen 60 may be detected.

Figure 4A:
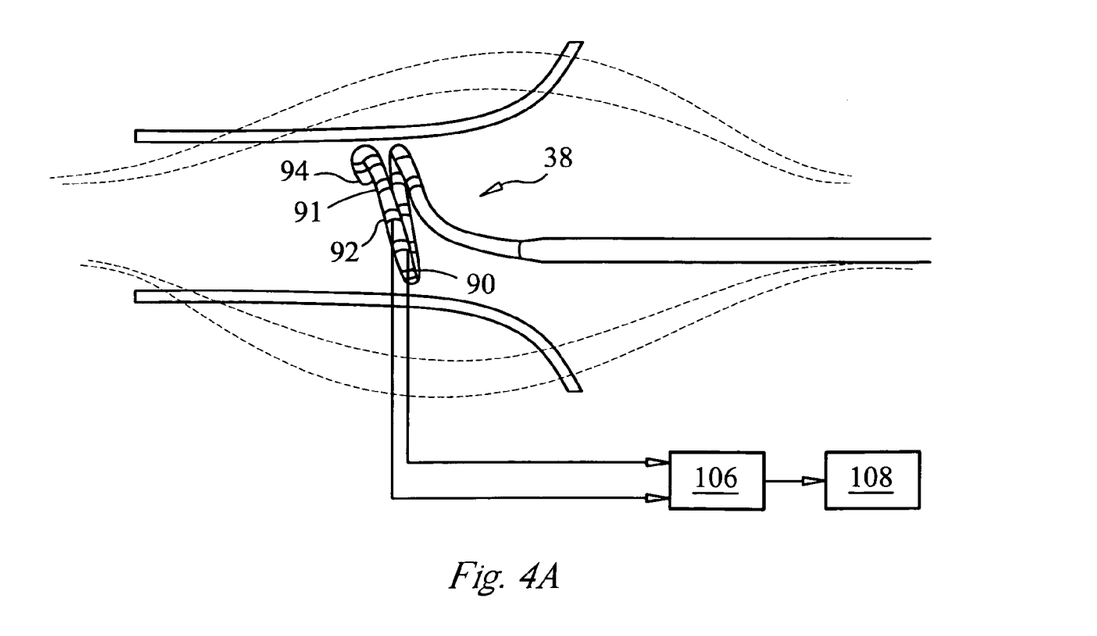
FIG. 4A illustrates an embodiment of a catheter in a deflected configuration and positioned near a treatment site.

FIG. 4A illustrates another embodiment of the thermally conductive region 38 of catheter 34 positioned near a treatment tissue site, such as in a pulmonary vein. In this embodiment the thermally conductive region 38 is shown as having a thermally conductive non-balloon element with a plurality of electrodes 90, 91, 92, 94, etc., wherein the thermally conductive region 38 is in a spiral or coiled configuration. Each of the plurality of electrodes may be monitored by the impedance measurement system 106, which can provide information about each electrode's baseline impedance that will vary as the thermally conductive region 38 contacts the targeted treatment tissue. The impedance measurement system 106 may use an impedance multiplexer to measure the impedance (voltages) between the electrodes of the thermally conductive region 38 by scanning the electrodes and recording all the impedance voltages. For example, an excitation current may be applied between electrodes 94 and 92 and the impedance voltage may be measured between electrodes 90 and 91. Next an excitation current may be applied between electrodes 90 and 93 and the impedance voltage may be measured between electrodes 91 and 92. This process may continue until impedance measurements are calculated for various combinations of electrodes.

The measured impedance voltages may be processed by using a signal processor 108 that can extract relevant data from a specific frequency range to correlate the impedance change for each electrode to that electrode's contact with the target treatment tissue. The impedance associated with those electrodes in contact with the tissue will be higher than those that are surrounded by the blood pool. Accordingly, the electrodes with the highest impedance will be the ones in best contact with the target treatment tissue, and as a result should provide the orientation of the catheter tip to the treatment tissue site.

Figure 4B:
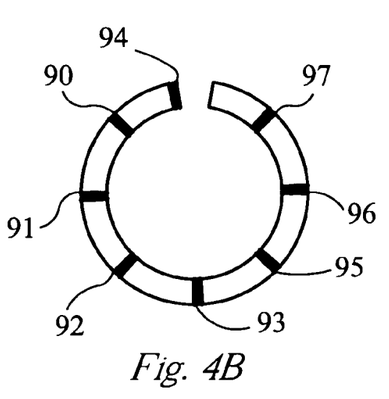
FIG. 4B illustrates an embodiment of the catheter tip of FIG. 4A having four electrodes in its thermally-transmissive region.
Figure 4C:
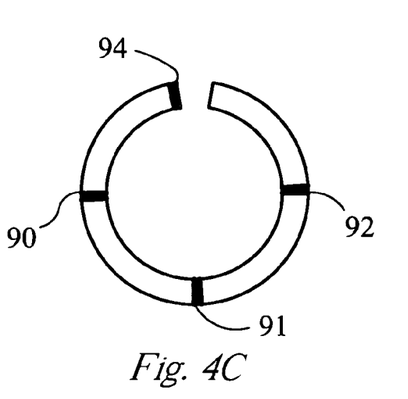
FIG. 4C illustrates an embodiment the catheter tip of FIG. 4A having eight electrodes in its thermally-transmissive region.

FIG. 4B illustrates an embodiment of the thermally conductive region 38 of catheter 34 having four electrodes 90, 91, 92 and 94. FIG. 4C illustrates another embodiment of the thermally conductive region 38 of catheter 34 having eight electrodes 90, 91, 92, 93, 94, 95, 96 and 97. The number of electrodes controls the accuracy of the contract assessment of the catheter's thermally conductive region 38. As the number of electrodes placed on the catheter's thermally conductive region 38 increases, the more accurate the contact assessment measurement. In addition, besides providing contact assessment, this system, as well as all the other system embodiments, can also provide enhanced assessment of lesion quality and/or size. For example, by measuring the electrical impedance of tissue prior to a cryogenic treatment, and then measuring the electrical impedance of that tissue subsequent to cryogenic treatment, it is possible to quantify the amount of treated tissue for a particular treatment session or sessions.

Depending on the rate of change of the impedance, the cooling profile may be adjusted. For example, a cooling profile may be developed for an optimal treatment regime, where the preset impedances (e.g., Z1, Z2, Z3, and Z4) are desired at corresponding times (e.g., T1, T2, T3 and T4). As a specific time in the treatment regime is reached, the impedance is determined from a measured impedance voltage, and that impedance is compared to a preset impedance (e.g., Z1, Z2, Z3, and Z4). Depending on the measured impedance, the cooling profile may be adjusted to increase or decrease the cooling power of the catheter, thereby providing increased treatment regime control.

Figure 5:
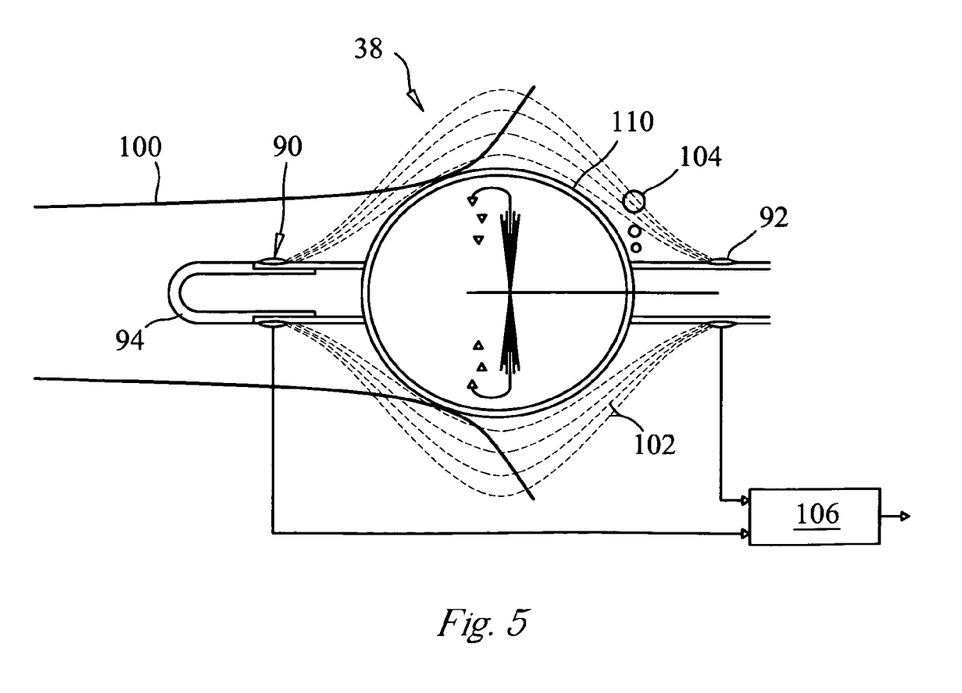
FIG. 5 illustrates an embodiment of a catheter for detecting fluid egress from a catheter.

The catheter, as illustrated in FIG. 5 can be used for detecting gas or liquid egress 104 from the catheter. After applying a low frequency electrical current (e.g., in the range of 250 Hz to 100 kHz) to the two electrodes 90, 92 the impedance can be measured by the impedance measurement system 106. The impedance measurement signal is then processed using a signal processor 108 that can extract relevant data from a specific frequency range to correlate the impedance change, if any, due to a gas egress into the blood stream. The application of the low frequency electrical current causes an electrical field 110 to form, which basically encloses or encompasses the thermally transmissive region 38. This electrical field 110 may have similar functionality to the expandable membrane 64, which is to provide leak detection in the event that the chamber or inside balloon 62 were to rupture, crack or leak. Thus, the electrical field 110 may be called a "virtual balloon" capable of detecting a fluid egress or expulsion 104 from the catheter 34 and generating a signal for automatic shutdown of the catheter system 30. Of course, unlike the leak detection of the expandable membrane 64, which measures ruptures or leaks internal to the catheter 34, the leak detection of electrical field 110 is external to the catheter 34, and found in the external fluid and tissue being treated. In those situations where fluid egress is present, a signal is generated to stop the flow of cryogenic fluid to the catheter and evacuate all fluid from the catheter.

In an alternative embodiment, additional electrodes 86 and 88 may be placed on the shaft of the catheter treatment section (similar to those shown in FIG. 2) to increase the sensitivity of the detection system, and thus provide for lower amplitude and/or lower frequency excitation signals to be used.

Figure 6:
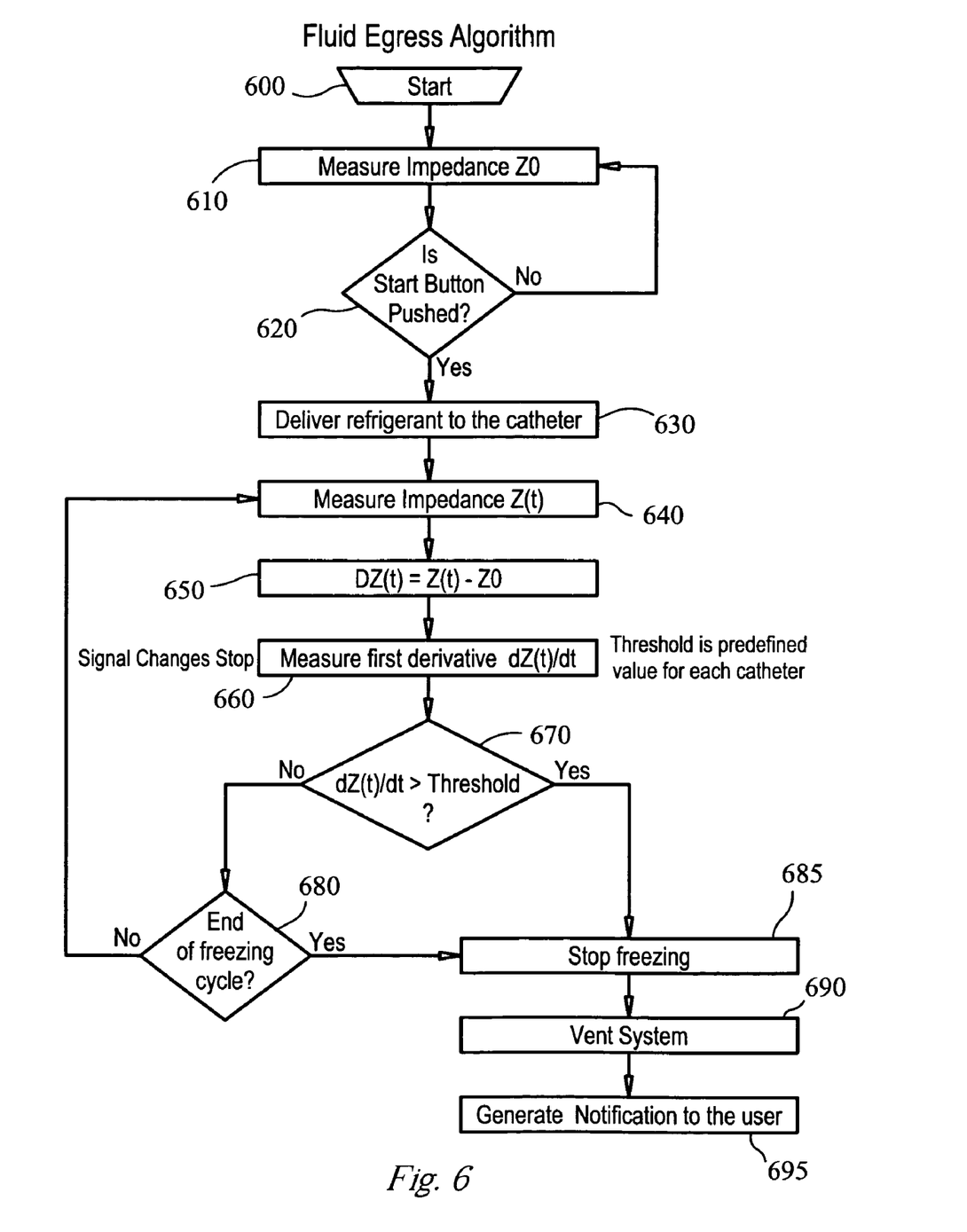
FIG. 6 illustrates an embodiment of a fluid egress algorithm.
Figure 7:
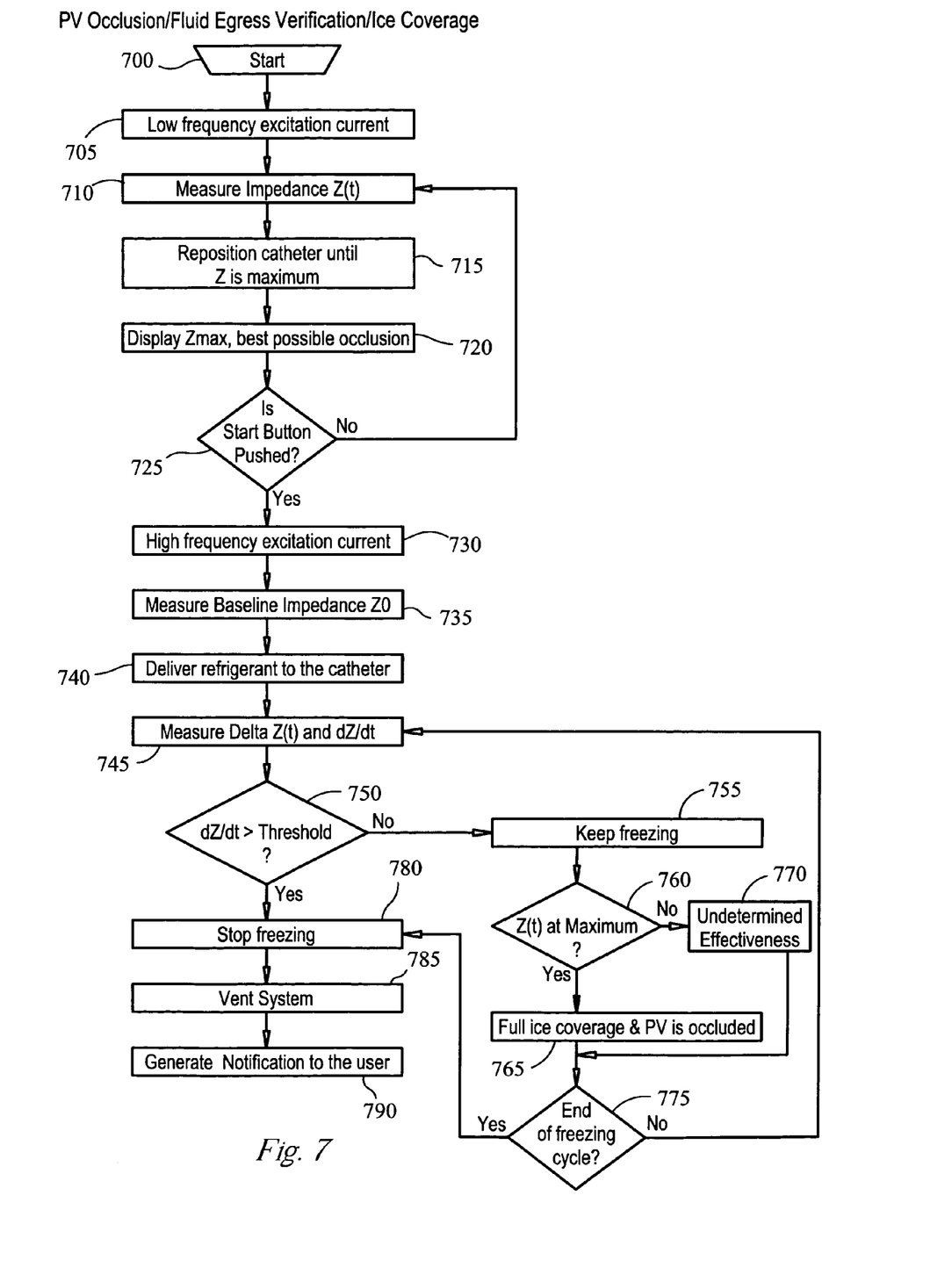
FIG. 7 illustrates an embodiment of a pulmonary vein occlusion/fluid egress/ice coverage verification algorithm.
Figure 8:
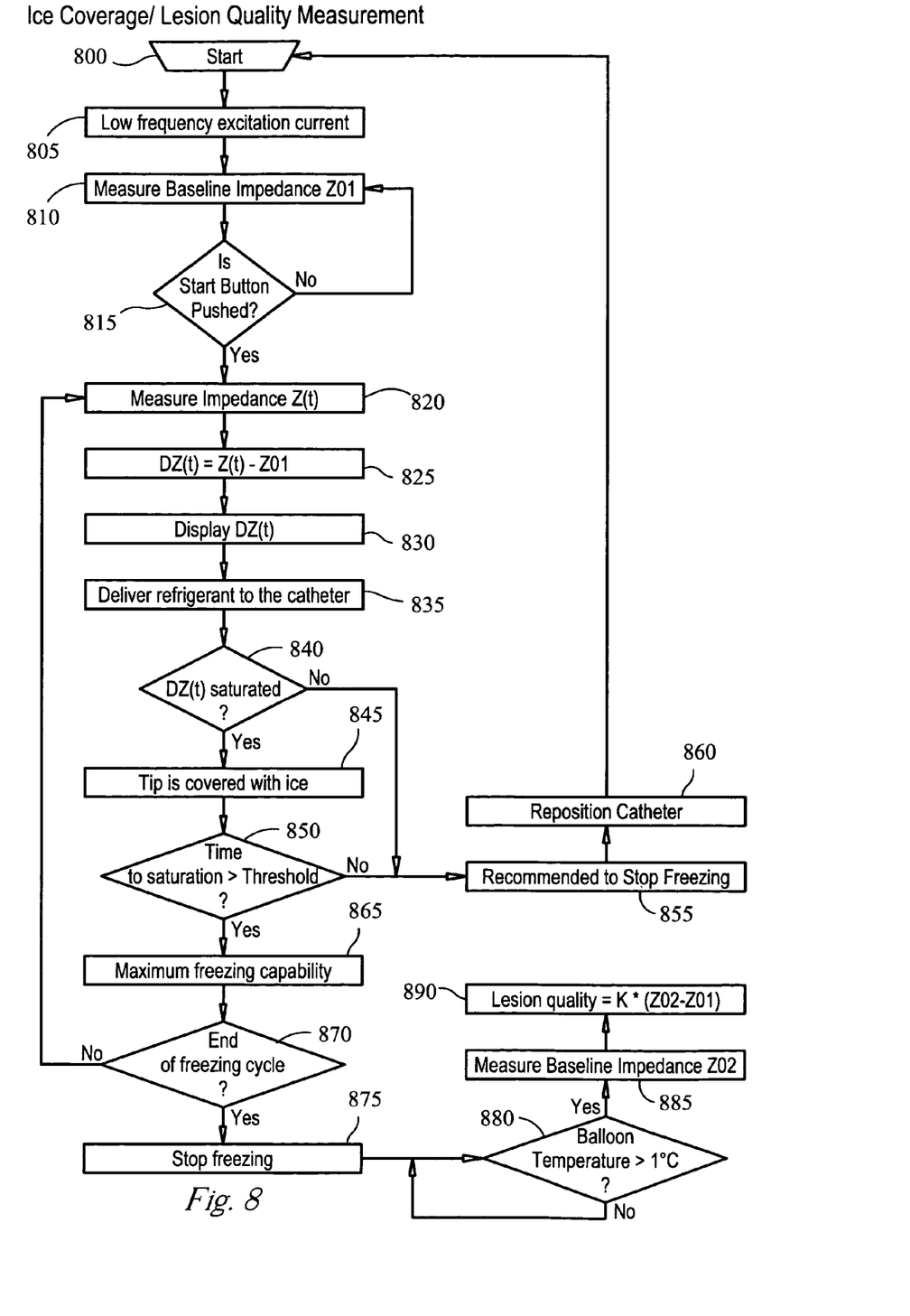
FIG. 8 illustrates an embodiment of a ice coverage/lesion quality measurement algorithm.

In conjunction with the various electrode configurations described above, there are various processing algorithms that may be employed. As illustrated in FIGS. 6, 7 and 8, processing algorithms for determining fluid egress, pulmonary vein occlusion/fluid egress verification and tip ice coverage/lesion quality measurement are provided.

Figure 10:
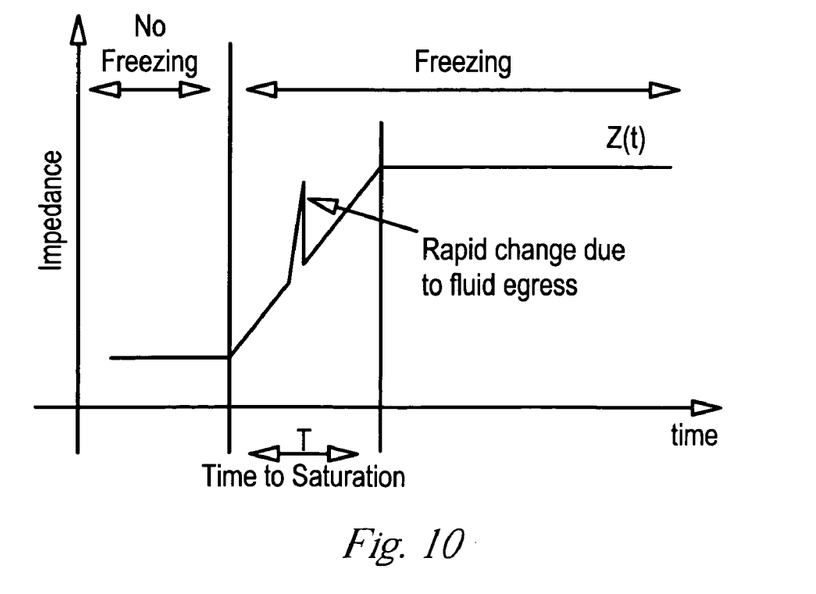
FIG. 10 illustrates a graph of the general impedance $Z(t)$ with an impedance spike due to a fluid egress.

Referring to FIG. 6, an exemplary fluid egress algorithm is illustrated. The process starts at step 600 and a baseline impedance $Z_0$ is measured across the measurement electrodes (step 610). If the start button for the treatment cycle has not been activated, then another baseline line impedance $Z_0$ may be measured. Upon the activation of the start button (step 620), the refrigerant is delivered to the catheter (step 630). After delivery of the refrigerant (coolant) (step 630), the impedance Z(t) (step 640) is measured and a delta impedance (D) Z(t) is calculated wherein the delta Z is the impedance Z at time t minus the baseline impedance $Z_0$ (step 650), DZ(t) =Z(t)-$Z_0$. In general, the baseline impedance $Z_0$ will increase at a linear rate as freezing of the treatment tissue occurs. For example, if $Z_0$ is first measured to be 20 ohms, and after application of a treatment cycle, the impedance Z is 25 ohms, then delta impedance DZ(t) is 5 ohms. However, if a fluid leak should occur, then the speed of the change with increase rapidly and cause a sudden spike in the impedance Z(t). The spike on the impedance graph shown in FIG. 10 illustrates this situation. In step 660, the signal changes will typical stop and the first derivative dZ(t)/dt is measured. If the dZ(t)/dt is greater than the threshold value, which is a predetermined value for each catheter, then the freezing cycle is halted (step 670). Otherwise, the system checks to determine if the treatment cycle has reached the end of the freezing cycle (step 680). If so, then the freezing is stopped (step 685) and the system is vented (step 690). After the system is vented (step 690), a notification is generated to the user (step 690).

Referring to FIG. 7, an exemplary balloon catheter controller algorithm for measuring pulmonary vein occlusion/fluid egress/ice coverage is illustrated. Steps 700 through 720 relate to assessing the quality of a pulmonary vein (PV) occlusion. The process commences at step 700 and a low frequency excitation current may be applied across a pair of electrodes (step 705). The impedance Z(t) is measured (step 710) and the catheter is repositioned until the impedance Z(t) is at a maximum, where the $Z_{max}$ may be displayed and serves to indicate that a best possible pulmonary vein occlusion has occurred. Upon the activation of the start button (step 725), a high frequency excitation current may be applied across a pair of electrodes (step 730), and the baseline line impedance $Z_0$ may be measured (step 735). The change to a high frequency excitation current facilitates the measurement of the bio-impedance across a treatment tissue site.

Figure 9:
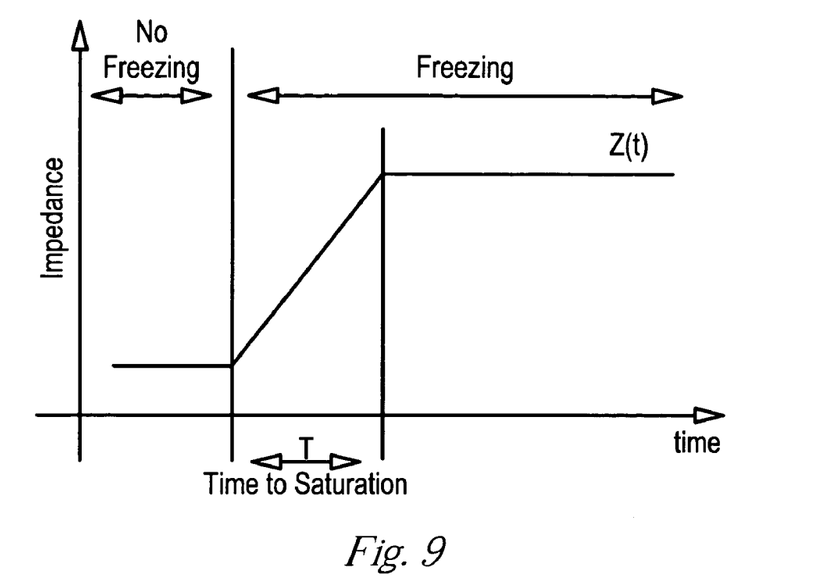
FIG. 9 illustrates a graph of the general impedance $Z(t)$ with respect to time.

After delivery of a refrigerant (coolant) to the catheter (step 740), the impedance Z(t) (step 745) is measured and a delta impedance (D) Z(t) is calculated wherein the delta Z is the impedance Z at time t minus the baseline impedance $Z_0$ (step 735) DZ(t)=Z(t)-$Z_0$. In step 745, the signal changes will typical stop and the first derivative dZ(t)/dt is calculated. If the dZ(t)/dt is greater than the threshold value, which is a predetermined value for each catheter, then the freezing cycle is halted (step 750). Otherwise, the system continues the freezing treatment (step 755) and checks to determine if the impedance Z(t) is at a maximum value (step 760). A graph of the general impedance Z(t) with respect to time is illustrated in FIG. 9. If the impedance Z(t) is at a maximum value, full ice coverage of catheter treatment tip has occurred and the PV has been occluded. If Z(t) is not at a maximum value, then the effectiveness of the treatment is undetermined (step 770). If the treatment cycle has reached the end of the freeing cycle (step 775), then the freezing is stopped (step 780) and the system is vented (step 785). After the system is vented (step 785), a notification is generated and sent to the user (step 790). Otherwise, the system will measure a new impedance Z(t) (step 745) and calculate a delta impedance (D) Z(t) wherein the delta Z is the impedance Z at time t minus the baseline impedance $Z_0$. In step 745, the signal changes will typical stop and the first derivative dZ(t)/dt is calculated. The process continues as discussed in steps 745 through 790 until the selected treatment is completed.

Referring to FIG. 8, an exemplary catheter controller algorithm for measuring catheter tip ice coverage/lesion quality is illustrated. The process commences at step 800 and a low frequency excitation current may be applied across a pair of electrodes (step 805). A baseline impedance $Z_{01}$ is measured (step 810). Upon the activation of the start button (step 815), the impedance Z(t) is measured. The delta impedance DZ(t) is calculated wherein the delta Z is the impedance Z at time t minus the first baseline impedance $Z_{01}$ (step 825). DZ(t)=Z(t)-$Z_{01}$. the value of delta impedance DZ(t) may be displayed (step 830). A refrigerant (coolant) is delivered to the catheter (step 835), The value of DZ(t) is processed to determine if DZ(t) has reached a saturated condition (step 840). If so, the catheter tip is covered with ice (step 845) and the time to saturation is compared to the time threshold (step 850). If not, a recommendation that the freezing procedure be halted (step 855), the catheter be repositioned (step 860) and the process restarted (step 800) is generated. If time to saturation is greater than the time threshold, a recommendation that the freezing procedure be halted (step 855), the catheter be repositioned (step 860) and the process restarted (step 800) is generated. If the time to saturation is less than the time threshold, then maximum freezing capability is requested (step 870).

If the treatment cycle has reached the end of the freeing cycle (step 870), then the freezing is stopped (step 875) and the temperature of the cooling segment is measured and compared to a temperature threshold (e.g., +1 degree C.) to determine if the catheter tip has warmed sufficiently to be removed from the tissue treatment site (step 880). If the temperature of the cooling segment is less than the temperature threshold (e.g., +1 degree C.), the catheter usually remains in its current position, and another temperature reading is taken. If the temperature of the cooling segment is greater than the temperature threshold (e.g., +1 degree C.), a new baseline impedance $Z_{02}$ is measured (step 885) and the lesion quality may be calculated (step 890) by the equation: lesion quality=K*$(Z_{02}-Z_{01})$; where K is a constant multiplier determined from in vitro testing or finite element model calculations and may have a specific value pre different catheter type (for e.g., a 6 mm long tip will usually have a different K than a 4 mm long tip).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for determining fluid egress comprising:
  positioning a catheter at a tissue treatment site, the catheter comprising:
    a shaft having a proximal portion, a distal tip, and at least one fluid pathway therebetween;
    an expandable element defining a cooling chamber therein in fluid communication with the at least one fluid pathway;
    a first electrode located on an exterior surface of the shaft between the proximal portion and the expandable element; and
    a second electrode located on the exterior surface of the shaft between the expandable element and the distal tip;
  applying an electrical current between the first and second electrodes to form an electrical field about the expandable element;
  measuring impedance between the first and second electrodes; and
  correlating the measured impedance to a condition of fluid egress from the cooling chamber to a point exterior to the catheter, and generating a signal indicating the condition of fluid egress from the cooling chamber to the point exterior to the catheter.

2. The method of claim 1, wherein correlating the measured impedance includes:
  establishing a normal impedance range;
  comparing the measured impedance to the normal impedance range; and
  generating a signal if the measured impedance is outside of the normal impedance range.

3. The method of claim 1, wherein the electrical current is a low frequency signal.

4. The method of claim 1, wherein correlating the measured impedance is performed by a microprocessor.

5. The method of claim 1, wherein measuring impedance is performed by an impedance measuring circuit.

* * * * *